US008921267B2

(12) United States Patent
Satchivi et al.

(10) Patent No.: US 8,921,267 B2
(45) Date of Patent: Dec. 30, 2014

(54) SAFENING 6-(TRISUBSTITUTED PHENYL)-4-AMINO-2-PYRIDINECARBOXYLATE HERBICIDE INJURY ON CEREAL CROPS

(71) Applicant: Dow AgroSciences LLC, Indianapolis, IN (US)

(72) Inventors: Norbert M. Satchivi, Westfield, IN (US); Paul R. Schmitzer, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/919,416

(22) Filed: Jun. 17, 2013

(65) Prior Publication Data
US 2013/0281293 A1 Oct. 24, 2013

Related U.S. Application Data

(63) Continuation of application No. 12/620,869, filed on Nov. 18, 2009, now Pat. No. 8,530,383.

(60) Provisional application No. 61/117,332, filed on Nov. 24, 2008.

(51) Int. Cl.
| | | |
|---|---|---|
| A01N 25/32 | (2006.01) | |
| A01N 47/28 | (2006.01) | |
| A01N 37/18 | (2006.01) | |
| A01N 43/40 | (2006.01) | |

(52) U.S. Cl.
CPC ............... *A01N 25/32* (2013.01); *A01N 43/40* (2013.01)
USPC ........... 504/105; 504/106; 504/108; 504/148; 504/149

(58) Field of Classification Search
None
See application file for complete search history.

(56) References Cited

U.S. PATENT DOCUMENTS

| | | | |
|---|---|---|---|
| 4,902,340 A | 2/1990 | Hubele | |
| 5,393,734 A | 2/1995 | Andrea et al. | |
| 7,314,849 B2 * | 1/2008 | Balko et al. | 504/244 |

FOREIGN PATENT DOCUMENTS

| | | |
|---|---|---|
| UA | 41866 C2 | 10/2001 |
| WO | WO9418836 | 9/1994 |
| WO | WO2007/082098 | 7/2007 |
| WO | WO2009/029518 | 3/2009 |
| WO | WO 2009029518 * | 3/2009 |
| WO | WO2010/059671 | 5/2010 |
| WO | WO2010/059676 | 5/2010 |
| WO | WO2010/059680 | 5/2010 |
| WO | WO2010/060581 | 6/2010 |

OTHER PUBLICATIONS

Robinson, Darren K. et al, "Safening Influence of LAB 145138 on Nicosulfuron, Terbufos and Bentazon Interactions in Sweet Corn (*Zea mays*)." Weed Science, vol. 44, No. 2 (Apr.-Jun. 1996), pp. 339-344.

Kotoula-Syka, Eleni, et al."Interactions between SAN 582H and Selected Safeners on Grain Sorghum (*Sorghum bicolor*) and Corn (*Zea mays*)." Weed Technology, vol. 10, No. 2 (Apr.-Jun. 1996), pp. 299-304.

Hatzios, Kriton K. "Potential safeners for protecting sorghum (*Sorghum bicolor* (L.) Moench) against chlorsulfuron, fluazifop-butyl and sethoxydim." Weed Research, 1984, vol. 24, pp. 249-254.

Frazier, Todd L, Nissen, Scott J., "Influence of Crop Safeners on the Interaction of Primisulfurlon and Terbufos in Corn (*Zea mays*)." Weed Science, vol. 42, No. 2 (Apr.-Jun. 1994), pp. 168-171.

International Searching Authority, International Search Report and Written Opinion for PCT/US2009/064920, dated Sep. 2011.

International Searching Authority, International Preliminary Report on Patentability for PCT/US2009/064920, dated Oct. 2011.

* cited by examiner

*Primary Examiner* — Alton Pryor

(74) *Attorney, Agent, or Firm* — Michael R. Asam; Faegre Baker Daniels LLP

(57) ABSTRACT

Herbicidal injury caused by 6-(trisubstituted phenyl)-4-amino-2-pyridinecarboxylates in wheat and barley is reduced with the use of AD67 (MON 4660), benoxacor, 2-CBSU, daimuron, dichlormid, dicyclonon (BAS 145 138H), fenchlorazole-ethyl, fenclorim, fluxofenim, furilazole (MON 13900), glyphosate, isoxadifen-ethyl, mefenpyr-diethyl, naphthalic anhydride, oxabetrinil and mixtures thereof.

20 Claims, No Drawings

SAFENING 6-(TRISUBSTITUTED PHENYL)-4-AMINO-2-PYRIDINECARBOXYLATE HERBICIDE INJURY ON CEREAL CROPS

CROSS-REFERENCE TO RELATED APPLICATIONS

This application is a continuation application of U.S. patent application Ser. No. 12/620,869, filed Nov. 18, 2009, which claims priority to U.S. Provisional Application Ser. No. 61/117,332 filed Nov. 24, 2008, the disclosures of which are expressly incorporated herein by reference.

FIELD OF THE INVENTION

This invention concerns the safening of the herbicidal injury caused by 6-(trisubstituted phenyl)-4-amino-2-pyridinecarboxylates in cereal crops.

BACKGROUND OF THE INVENTION

When agrochemicals, such as plant protection agents and especially herbicides, are used, the cultivated plants may be damaged to a certain degree, depending on factors such as the dose of agrochemicals and their method of application, the species of cultivated plant, the nature of the soil and climatic conditions, for example, length of time of exposure to light, temperature and amounts of precipitation. Thus, it is known that cultivated plants which are to be protected from the adverse effect of undesirable plant growth may be damaged to a certain degree when an effective dose of herbicide is used. Various substances which are capable of specifically preventing the adverse effect of an herbicide on the cultivated plants, i.e. of protecting the cultivated plants without at the same time noticeably influencing the herbicidal action on weeds to be combated, have been proposed to solve this problem. However, it has been found that the antidotes proposed frequently have only a narrow field of use, i.e., a particular antidote is frequently suitable only for use with individual species of cultivated plants and/or for protecting the cultivated plants from individual herbicidal substances or classes of substances.

U.S. Pat. No. 7,314,849 B2 describes certain 6-(polysubstituted aryl)-4-amino-2-pyridinecarboxylate compounds and their use as herbicides. While certain of these compounds have been shown to be particularly effective herbicides for controlling undesirable vegetation in cereal crops, they have also been shown to produce slight amounts of damage to both wheat and barley at concentrations required to adequately control the undesirable vegetation.

SUMMARY OF THE INVENTION

It has now been found that, surprisingly, the phytotoxic effect of certain 6-(poly-substituted aryl)-4-amino-2-pyridinecarboxylate compounds, which have an auxinic mode of action, on wheat and barley can be ameliorated by the use of certain safeners. The present invention concerns a method of protecting cereal crops from the harmful effects of a 6-(trisubstituted phenyl)-4-amino-2-pyridinecarboxylate herbicide of the formula (I)

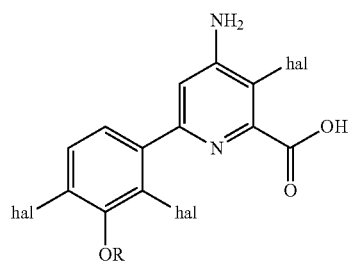

wherein hal represents F, Cl or Br, and R represents methyl or ethyl,
and its agriculturally acceptable salt, ester and amide derivatives which comprises contacting wheat and barley with, or applying to the area under cultivation, a safener, or a compatible herbicide capable of safening, selected from the group consisting of AD67 (MON 4660), benoxacor, 2-CBSU, daimuron, dichlormid, dicyclonon (BAS 145 138H), fenchlorazole-ethyl, fenclorim, fluxofenim, furilazole (MON 13900), glyphosate, isoxadifen-ethyl, mefenpyr-diethyl, naphthalic anhydride, oxabetrinil and mixtures thereof.

The present invention also concerns a composition for protecting wheat and barley from the harmful effects of a 6-(trisubstituted phenyl)-4-amino-2-pyridinecarboxylate herbicide of the formula (I)

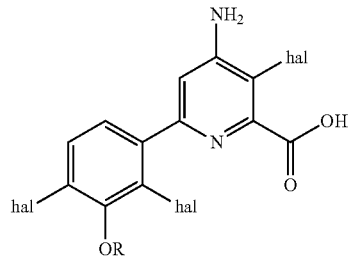

wherein hal represents F, Cl or Br, and R represents methyl or ethyl,
and its agriculturally acceptable salt, ester and amide derivatives which comprises, in addition to the 6-(trisubstituted phenyl)-4-amino-2-pyridinecarboxylate herbicide, a safener or compatible herbicide capable of safening selected from the group consisting of AD67 (MON4660), benoxacor, 2-CBSU, daimuron, dichlormid, dicyclonon (BAS 145 138H), fenchlorazole-ethyl, fenclorim, fluxofenim, furilazole (MON 13900), glyphosate, isoxadifen-ethyl, mefenpyr-diethyl, naphthalic anhydride, oxabetrinil, and mixtures thereof. In preferred compositions, the 6-(trisubstituted phenyl)-4-amino-2-pyridinecarboxylate herbicide is a 4-amino-3-chloro-6-(4-chloro-2-fluoro-3-methoxyphenyl)-2-pyridinecarboxylic acid derivative or a 4-amino-3-chloro-6-(2,4-dichloro-3-methoxyphenyl)-2-pyridinecarboxylic acid derivative.

It has been surprisingly found that the use of a spirooxazolidine safener such as AD 67 (MON 4660) in composition with a pyridinecarboxylate herbicide of the formula (I) exhibits a protecting effect against the phytotoxicity of the pyridinecarboxylate herbicide of formula (I) on wheat (*Triticum aestivum* L; TRZAS) and barley (*Hordeum vulgare* L; HORVS) without losing the herbicidal effects on weeds such as cleavers (*Galium aparine* L; GALAP), purple deadnettle (*Lamium purpureum* L; LAMPU), corn poppy (*Papaver rhoeas* L; PAPRH).

The combinations of dichloroacetamide safeners such as benoxacor, dichlormid, dicyclonon (BAS 145 138H), furilazole (MON 13900) and a pyridinecarboxylate herbicide of formula (I) resulted in an unexpected safening effect against the phytotoxicity of the pyridinecarboxylate herbicide of formula (I) on wheat (*Triticum aestivum* L; TRZAS) and barley (*Hordeum vulgare* L; HORVS) without reduction of the herbicidal effects on weeds such as cleavers (*Galium aparine* L; GALAP), purple deadnettle (*Lamium purpureum* L; LAMPU), corn poppy (*Papaver rhoeas* L; PAPRH), chickweed (*Stellaria media* L; STEME), bird's-eye speedwell (*Veronica persica* L; VERPE).

It has also been surprisingly found that a mixture of a benzenesulfonamide safener such as 2-CBSU and a pyridinecarboxylate herbicide of formula (I) exhibits a safening effect against the phytotoxicity of the pyridinecarboxylate herbicide of formula (I) on wheat (*Triticum aestivum* L; TRZAS) and barley (*Hordeum vulgare* L; HORVS) without losing the herbicidal effects on weeds such as cleavers (*Galium aparine* L; GALAP), purple deadnettle (*Lamium purpureum* L; LAMPU), corn poppy (*Papaver rhoeas* L; PAPRH).

It has also been unexpectedly found that the mixture of phenyl pyrazole safeners such as fenchlorazole-ethyl, mefenpyr-diethyl and a pyridinecarboxylate herbicide of formula (I) shows a safening effect against the phytotoxicity of the pyridinecarboxylate herbicide of formula (I) on wheat (*Triticum aestivum* L; TRZAS) and barley (*Hordeum vulgare* L; HORVS) without reducing the herbicidal effects on weeds such as cleavers (*Galium aparine* L; GALAP), purple deadnettle (*Lamium purpureum* L; LAMPU), corn poppy (*Papaver rhoeas* L; PAPRH), bird's-eye speedwell (*Veronica persica* L; VERPE), Russian thistle (*Salsola iberica* L; SASKR), wild pansy (*Viola tricolor* L; VIOTR).

The combination of a phenylpyrimidine safener such as fenclorim and a pyridinecarboxylate herbicide of formula (I) exhibits a safening effect against the phytotoxicity of the pyridinecarboxylate herbicide of formula (I) on wheat (*Triticum aestivum* L; TRZAS) and barley (*Hordeum vulgare* L; HORVS) without losing the herbicidal effects on weeds such as cleavers (*Galium aparine* L; GALAP), purple deadnettle (*Lamium purpureum* L; LAMPU), corn poppy (*Papaver rhoeas* L; PAPRH), wild buckwheat (*Polygonum convolvulus* L; POLCO).

The combinations of safeners of the oxime class such as fluxofenim, oxabetrinil and a pyridinecarboxylate herbicide of formula (I) have resulted in an unexpected safening effect against the phytotoxicity of the pyridinecarboxylate herbicide of formula (I) on wheat (*Triticum aestivum* L; TRZAS) and barley (*Hordeum vulgare* L; HORVS) without reduction of the herbicidal effects on weeds such as cleavers (*Galium aparine* L; GALAP), purple deadnettle (*Lamium purpureum* L; LAMPU), corn poppy (*Papaver rhoeas* L; PAPRH), scented mayweed (*Matricaria chamomila* L; MATCH), Russian thistle (*Salsola iberica* L; SASKR).

It has been also surprisingly found that the mixture of oxime ether safeners, such as isoxadifen-ethyl, and a pyridinecarboxylate herbicide of formula (I) shows a safening effect against the phytotoxicity of the pyridinecarboxylate herbicide of formula (I) on wheat (*Triticum aestivum* L; TRZAS), durum wheat (Triticum durum L; TRZDU), and barley (*Hordeum vulgare* L; HORVS) without reducing the herbicidal effects on weeds such as purple deadnettle (*Lamium purpureum* L; LAMPU), corn poppy (*Papaver rhoeas* L; PAPRH).

The mixture of a naphthopyranone safener such as naphthalic anhydride and a pyridinecarboxylate herbicide of formula (I) shows an unexpected safening effect against the phytotoxicity of the pyridinecarboxylate herbicide of formula (I) on wheat (*Triticum aestivum* L; TRZAS) and barley (*Hordeum vulgare* L; HORVS) without reduction of the herbicidal effects on weeds such as cleavers (*Galium aparine* L; GALAP), purple deadnettle (*Lamium purpureum* L; LAMPU), corn poppy (*Papaver rhoeas* L; PAPRH), kochia (*Kochia scoparia* L; KCHSC), wild pansy (*Viola tricolor* L; VIOTR).

It has also been unexpectedly found that the mixture of a pyridinecarboxylate herbicide of formula (I) and a phenylurea herbicide such as daimuron exhibits a surprising safening effect against the phytotoxicity of the pyridinecarboxylate herbicide of formula (I) on wheat (*Triticum aestivum* L; TRZAW), durum wheat (Triticum durum L; TRZDU), and barley (*Hordeum vulgare* L; HORVS) without reducing the herbicidal effects on weeds such as purple deadnettle (*Lamium purpureum* L; LAMPU), corn poppy (*Papaver rhoeas* L; PAPRH).

It has been also surprisingly found that the mixture of a pyridinecarboxylate herbicide of the formula (I) and an EPSP (5-enolpyruvylshikimate-3-phosphate) synthase inhibitor herbicide such as glyphosate exhibits an unexpected safening effect against the phytotoxicity on wheat (*Triticum aestivum* L; TRZAS) and barley (*Hordeum vulgare* L; HORVS).

DETAILED DESCRIPTION OF THE INVENTION

The pyridinecarboxylates of formula I are a new class of compounds having herbicidal activity. A number of pyridinecarboxylate compounds are described in U.S. Pat. No. 7,314,849, including 4-amino-3-chloro-6-(4-chloro-2-fluoro-3-methoxyphenyl)pyridine-2-carboxylic acid (compound 1) and 4-amino-3-chloro-6-(2,4-dichloro-3-methoxyphenyl)-pyridine-2-carboxylic acid (compound 2). The pyridinecarboxylates of formula (I) control annual grass weeds and broadleaf weeds in wheat and barley but are also phytotoxic to wheat and barley at commercially herbicidal doses.

AD67 (MON 4660) is the common name for 4-(dichloroacetyl)-1-oxa-4-azaspiro[4,5]decane. Its safening activity is described in *The Pesticide Manual*, Thirteenth Edition, 2003. AD67 (MON 4660) is used as a safener in maize.

Benoxacor is the common name for (±)-4-(dichloroacetyl)-3,4-dihydro-3-methyl-2H-1,4-benzoxazine. Its safening activity is described in *The Pesticide Manual*, Fourteenth Edition, 2006. Benoxacor is used as a safener in maize.

2-CBSU is the common name for N-(aminocarbonyl)-2-chlorobenzenesulfonamide. Its safening activity is described in *Modern Crop Protection Compounds*, 2007. 2-CBSU has been shown to safen herbicidal injury in maize.

Daimuron is the common name for N-(4-methylphenyl)-N'-(1-methyl-1-phenylethyl)urea. Its herbicidal activity is described in *The Pesticide Manual*, Fourteenth Edistion, 2006. Daimuron is used as a selective herbicide of cyperaceous weeds and annual grass weeds in paddy rice.

Dichlormid is the common name for N,N-diallyl-2,2-dichloroacetamide. Its safening activity is described in *The Pesticide Manual*, Fourteenth Edition, 2006. Dichlormid is used as a safener for maize and sorghum.

Dicyclonon (BAS 145 138H) is the common name for (RS)-1-dichloroacetyl-3,3,8a-trimethylperhydropyrrolo[1,2]

pyrimidin-6-one. Its safening activity is described in *Pesticide Biochemistry and Physiology* 1992, 42, 128-139. Dicyclonon (BAS 145 138H) is used as a safener for maize.

Fenchlorazole is the common name for 1-(2,4-dichlorophenyl)-5-(trichloromethyl)-1H-1,2,4-triazole-3-carboxylic acid. Its safening activity is described in *The Pesticide Manual*, Fourteenth Edition, 2006. Fenchlorazole is used as a safener in wheat, rye and triticale.

Fenclorim is the common name for 4,6-dichloro-2-phenylpyrimidine. Its safening activity is described in *The Pesticide Manual*, Fourteenth Edition, 2006. Fenclorim is used as a safener in direct-seeded rice.

Fluxofenim is the common name for 1-(4-chlorophenyl)-2,2,2-trifluoroethanone O-(1,3-dioxolan-2-ylmethyl)oxime. Its safening activity is described in *The Pesticide Manual*, Fourteenth Edition, 2006. Fluxofenim is used as a safener in sorghum.

Furilazole (MON 13900) is the common name for 3-(dichloroacetyl)-5-(2-furanyl)-2,2-dimethyloxazolidine. Its safening activity is described in *The Pesticide Manual*, Fourteenth Edition, 2006. Furilazole (MON 13900) is used as a safener in maize.

Isoxadifen-ethyl is the common name for ethyl 4,5-dihydro-5,5-diphenyl-3-isoxazolecarboxylate. Its safening activity is described in *The Pesticide Manual*, Fourteenth Edition, 2006. Isoxadifen is used as a safener in maize.

Glyphosate is the common name for N-(phosphonomethyl)glycine. Its herbicidal activity is described in *The Pesticide Manual*, Fourteenth Edition, 2006. Glyphosate controls a wide range of annual and perennial, broadleaf and grass weeds.

Mefenpyr is the common name for 1-(2,4-dichlorophenyl)-4,5-dihydro-5-methyl-1H-pyrazole-3,5-dicarboxylic acid. Its safening activity is described in *The Pesticide Manual*, Fourteenth Edition, 2006. Mefenpyr is used as a safener in wheat, rye, triticale and barley.

Naphthalic anhydride is the common name for 1H,3H-naphtho[1,8-cd]pyran-1,3-dione. Its safening activity is described in *The Pesticide Manual*, Eighth Edition, 1987. Naphthalic anhydride is used as a safener in maize and sorghum.

Oxabetrinil is the common name for α-[(1,3-dioxolan-2-yl)methoxyimino]benzene-acetonitrile. Its safening activity is described in *The Pesticide Manual*, Fourteenth Edition, 2006. Oxabetrinil is used as a safener in sorghum.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation. The term safener, as used herein, refers to a compound that selectively protects crop plants from herbicide damage without significantly reducing activity in target weed species.

Herbicidal activity is exhibited by the compounds when they are applied directly to the plant or to the locus of the plant via foliar, soil, or water application at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

Cultivated plants which are to be protected from the adverse effect of undesirable plant growth may be damaged to a certain degree when an effective dose of herbicides is used. Safening means preventing the adverse effect of an herbicide on the cultivated plants, i.e., protecting the cultivated plants without, at the same time, noticeably influencing the herbicidal action on weeds to be combated.

In the composition of this invention, the weight ratio of the safener to the pyridinecarboxylate of formula (I) at which the herbicidal effect on the cultivated plant is safened lies within the range of between about 16:1 and about 1:32. Preferably, the weight ratio of the safener to the pyridinecarboxylate of formula (I) at which the herbicidal effect on the cultivated plant is safened lies within the range of between about 4:1 and about 1:8.

The rate at which the safened composition is applied will depend upon the particular type of weed to be controlled, the degree of control required, and the timing and method of application. In general, the composition of the invention can be applied at an application rate of between about 4 grams per hectare (g/ha) and about 1200 g/ha based on the total amount of pyridinecarboxylate of formula (I) and safener in the composition.

The pyridinecarboxylate of formula (I) and the safener of the present invention can be applied either separately or together as part of a multipart herbicidal system.

The herbicide-safener mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the safened composition of the present invention include: 2,4-D esters and amines, acetochlor, acifluorfen, aclonifen, AE0172747, alachlor, aminocyclopyrachlor, amidosulfuron, aminotriazole, ammonium thiocyanate, anilifos, atrazine, AVH 301, azimsulfuron, benfuresate, bensulfuron-methyl, bentazone, benthiocarb, benzobicyclon, bifenox, bispyribac-sodium, bromacil, bromoxynil, butachlor, butafenacil, butralin, cafenstrole, carbetamide, carfentrazone-ethyl, chlorflurenol, chlorimuron, chlorpropham, cinosulfuron, clethodim, clomazone, clopyralid, cloransulam-methyl, cyclosulfamuron, cycloxydim, cyhalofop-butyl, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ET-751, ethoxysulfuron, ethbenzanid, F7967, fenoxaprop, fenoxaprop-ethyl, fentrazamide, flazasulfuron, florasulam, fluazifop, fluazifop-P-butyl, flucetosulfuron, flufenacet, flufenpyr-ethyl, flumetsulam, flumiclorac-pentyl, flumioxazin, fluometuron, flupyrsulfuron, fluoroxypyr, fomesafen, foramsulfuron, fumiclorac, glufosinate, glufosinate-ammonium, glyphosate, halosulfuron, haloxyfop-methyl, haloxyfop-R, imazamethabenz, imazamox, imazapic, imazapyr, imazaquin, imazethapyr, imazosulfuron, indanofan, iodosulfuron, ioxynil, IR 5790, isoproturon, isoxaben, isoxaflutole, KUH-021, lactofen, linuron, MCPA, MCPA ester & amine, mecoprop-P, mefenacet, mesosulfuron, mesotrione, metamifop, metolachlor, metosulam, metribuzin, metsulfuron, molinate, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, penoxsulam, pentoxazone, pethoxamid, picloram, picolinafen, piperophos, pretilachlor, profoxydim, propachlor, propanil, propyzamide, prosulfocarb, prosulfuron, pyraclonil, pyrasulfotole, pyrazogyl, pyrazosulfuron, pyribenzoxim, pyriftalid, pyriminobac-methyl, primisulfuron, pyroxsulam, quinclorac, quizalofop-ethyl-D, S-3252, saflufenacil, sethoxydim, simazine, SL-0401, SL-0402, s-metolachlor, sulcotrione, sulfentrazone, sulfosate, tebuthiuron, terbacil, TH-547, thiazopyr, thiobencarb, triclopyr, triclopyr esters and amine, trifluralin and tritosulfuron.

The safened composition of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the herbicide-safener mixture of the present invention in combination with herbicides that are selective for the crop being treated and which complement the spectrum of weeds controlled by these compounds at the application rate employed. It is further generally preferred to apply the safened composition of the present invention and other complementary herbicides at the same time, either as a combination formulation or as a tank mix.

In practice, it is preferable to use the safened composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cotton seed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicide-safener mixture of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, or irrigation water, and by other conventional means known to those skilled in the art.

The following examples illustrate the present invention.

Evaluation of Postemergence Herbicidal Safening in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Weighed amounts of esters (methyl) or salts (TEA [triethylammonium], K [potassium]) of 4-amino-3-chloro-6-(4-chloro-2-fluoro-3-methoxyphenyl)pyridine-2-carboxylic acid (Compound 1) were dissolved in a volume of 97:3 volume/volume (v/v) acetone/dimethylsulfoxide (DMSO) to obtain stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 mL application volume at a rate of 187 liters per hectare (L/ha). Stocks solutions of the safeners were prepared following the same procedure. Spray solutions of the safeners and experimental compound mixtures were prepared by adding the stock solutions to the appropriate amount of dilution solution to form a 12 mL spray solution with active ingredients in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 1 through Table 22.

TABLE 1

Safening Activity of Herbicidal Compositions on Wheat and Barley

| Application Rate (g/ha) | | | TRZAS | | HORVS | | GALAP | | KCHSC | | LAMPU | | MATCH | |
|---|---|---|---|---|---|---|---|---|---|---|---|---|---|---|
| Compound | | Herbicide:Safener | | | | | | | | | | | | |
| 1 TEA salt | AD67 | Ratio | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | — | | — | | — | |
| 0 | 70 | | 0 | — | 0 | — | 0 | — | — | | — | | — | |
| 0 | 35 | | 0 | — | 0 | — | 0 | — | — | | — | | — | |
| 0 | 17.5 | | 0 | — | 0 | — | 0 | — | — | | — | | — | |
| 140 | 140 | 1:1 | 10 | 26 | 6 | 16 | 100 | 100 | 83 | 94 | 100 | 99 | 80 | 80 |
| 140 | 70 | 2:1 | 11 | 26 | 9 | 16 | 100 | 100 | 75 | 94 | 99 | 99 | 63 | 80 |
| 140 | 35 | 4:1 | 10 | 26 | 0 | 16 | 100 | 100 | 95 | 94 | 99 | 99 | 73 | 80 |

| Application Rate (g/ha) | | | PAPRH | | POLCO | | SASKR | | STEME | | VERPE | | VIOTR | |
|---|---|---|---|---|---|---|---|---|---|---|---|---|---|---|
| Compound | | Herbicide:Safener | | | | | | | | | | | | |
| 1 TEA salt | AD67 | Ratio | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 100 | 100 | 85 | 88 | 88 | 94 | 89 | 85 | 58 | 69 |
| 140 | 70 | 2:1 | 100 | 100 | 93 | 100 | 83 | 88 | 100 | 94 | 89 | 85 | 68 | 69 |
| 140 | 35 | 4:1 | 100 | 100 | 88 | 100 | 85 | 88 | 100 | 94 | 88 | 85 | 65 | 69 |

TABLE 2

Safening Activity of Herbicidal Compositions on Wheat and Barley

| Compound | | Application Rate (g/ha) Herbicide:Safener | TRZAS | | HORVS | | GALAP | | KCHSC | | LAMPU | | MATCH | |
|---|---|---|---|---|---|---|---|---|---|---|---|---|---|---|
| 1 TEA salt | Benoxacor | Ratio | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | — | — | — | — | — | — |
| 0 | 70 | | 0 | — | 0 | — | 0 | — | — | — | — | — | — | — |
| 0 | 35 | | 0 | — | 0 | — | 0 | — | — | — | — | — | — | — |
| 0 | 17.5 | | 0 | — | 0 | — | 0 | — | — | — | — | — | — | — |
| 140 | 140 | 1:1 | 7 | 26 | 5 | 16 | 100 | 100 | 91 | 94 | 100 | 99 | 78 | 80 |
| 140 | 70 | 2:1 | 14 | 26 | 7 | 16 | 100 | 100 | 96 | 94 | 100 | 99 | 90 | 80 |
| 140 | 35 | 4:1 | 20 | 26 | 0 | 16 | 100 | 100 | 96 | 94 | 100 | 99 | 80 | 80 |

| Compound | | Application Rate (g/ha) Herbicide:Safener | PAPRH | | POLCO | | SASKR | | STEME | | VERPE | | VIOTR | |
|---|---|---|---|---|---|---|---|---|---|---|---|---|---|---|
| 1 TEA salt | Benoxacor | Ratio | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 98 | 100 | 85 | 88 | 99 | 94 | 85 | 85 | 78 | 69 |
| 140 | 70 | 2:1 | 100 | 100 | 98 | 100 | 85 | 88 | 95 | 94 | 80 | 85 | 65 | 69 |
| 140 | 35 | 4:1 | 100 | 100 | 98 | 100 | 85 | 88 | 99 | 94 | 83 | 85 | 65 | 69 |

TABLE 3

Safening Activity of Herbicidal Compositions on Wheat and Barley

| Compound | | Application Rate (g/ha) Herbicide:Safener | TRZAS | | HORVS | | GALAP | | KCHSC | | LAMPU | | MATCH | |
|---|---|---|---|---|---|---|---|---|---|---|---|---|---|---|
| 1 TEA salt | 2-CBSU | Ratio | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | — | — | — | — | — | — |
| 0 | 70 | | 0 | — | 0 | — | 0 | — | — | — | — | — | — | — |
| 0 | 35 | | 0 | — | 0 | — | 0 | — | — | — | — | — | — | — |
| 0 | 17.5 | | 0 | — | 0 | — | 0 | — | — | — | — | — | — | — |
| 140 | 140 | 1:1 | 5 | 26 | 4 | 16 | 100 | 100 | 85 | 94 | 100 | 99 | 78 | 80 |
| 140 | 70 | 2:1 | 11 | 26 | 10 | 16 | 100 | 100 | 95 | 94 | 100 | 99 | 85 | 80 |
| 140 | 35 | 4:1 | 10 | 26 | 0 | 16 | 100 | 100 | 90 | 94 | 100 | 99 | 83 | 80 |

| Compound | | Application Rate (g/ha) Herbicide:Safener | PAPRH | | POLCO | | SASKR | | STEME | | VERPE | | VIOTR | |
|---|---|---|---|---|---|---|---|---|---|---|---|---|---|---|
| 1 TEA salt | 2-CBSU | Ratio | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 97 | 100 | 89 | 88 | 98 | 94 | 85 | 85 | 50 | 69 |
| 140 | 70 | 2:1 | 100 | 100 | 93 | 100 | 88 | 88 | 98 | 94 | 88 | 85 | 70 | 69 |
| 140 | 35 | 4:1 | 100 | 100 | 96 | 100 | 85 | 88 | 85 | 94 | 92 | 85 | 65 | 69 |

TABLE 4

Safening Activity of Herbicidal Compositions on Wheat and Barley

| Compound | Application Rate (g/ha) | Herbicide:Safener Ratio | TRZAS | | HORVS | | GALAP | | KCHSC | | LAMPU | | MATCH | |
|---|---|---|---|---|---|---|---|---|---|---|---|---|---|---|
| 1 TEA salt | Dichlormid | | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 15 | 26 | 20 | 16 | 100 | 100 | 100 | 94 | 100 | 99 | 73 | 80 |
| 140 | 70 | 2:1 | 6 | 26 | 15 | 16 | 100 | 100 | 85 | 94 | 100 | 99 | 84 | 80 |
| 140 | 35 | 4:1 | 7 | 26 | 0 | 16 | 100 | 100 | 83 | 94 | 100 | 99 | 73 | 80 |

| Compound | Application Rate (g/ha) | Herbicide:Safener Ratio | PAPRH | | POLCO | | SASKR | | STEME | | VERPE | | VIOTR | |
|---|---|---|---|---|---|---|---|---|---|---|---|---|---|---|
| 1 TEA salt | Dichlormid | | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 98 | 100 | 90 | 88 | 98 | 94 | 90 | 85 | 68 | 69 |
| 140 | 70 | 2:1 | 100 | 100 | 99 | 100 | 80 | 84 | 90 | 94 | 93 | 85 | 65 | 69 |
| 140 | 35 | 4:1 | 100 | 100 | 98 | 100 | 95 | 85 | 95 | 94 | 90 | 85 | 48 | 69 |

TABLE 5

Safening Activity of Herbicidal Compositions on Wheat and Barley

| Compound 1 | Application Rate (g/ha) | Herbicide:Safener Ratio | TRZAS | | HORVS | | GALAP | | KCHSC | | LAMPU | | MATCH | |
|---|---|---|---|---|---|---|---|---|---|---|---|---|---|---|
| TEA salt | Dicyclonon | | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | — | — | — | — | — | — |
| 0 | 70 | | 0 | — | 0 | — | 0 | — | — | — | — | — | — | — |
| 0 | 35 | | 0 | — | 0 | — | 0 | — | — | — | — | — | — | — |
| 0 | 17.5 | | 0 | — | 0 | — | 0 | — | — | — | — | — | — | — |
| 140 | 140 | 1:1 | 9 | 26 | 4 | 16 | 100 | 100 | 99 | 94 | 100 | 99 | 85 | 80 |
| 140 | 70 | 2:1 | 4 | 26 | 8 | 16 | 100 | 100 | 80 | 94 | 100 | 99 | 83 | 80 |
| 140 | 35 | 4:1 | 0 | 26 | 0 | 16 | 100 | 100 | 80 | 94 | 100 | 99 | 75 | 80 |

| Compound 1 | Application Rate (g/ha) | Herbicide:Safener Ratio | PAPRH | | POLCO | | SASKR | | STEME | | VERPE | | VIOTR | |
|---|---|---|---|---|---|---|---|---|---|---|---|---|---|---|
| TEA salt | Dicyclonon | | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 99 | 100 | 85 | 88 | 79 | 94 | 87 | 85 | 70 | 69 |
| 140 | 70 | 2:1 | 100 | 100 | 100 | 100 | 88 | 88 | 99 | 94 | 88 | 85 | 70 | 69 |
| 140 | 35 | 4:1 | 100 | 100 | 99 | 100 | 86 | 88 | 100 | 94 | 85 | 85 | 50 | 69 |

TABLE 6

Safening Activity of Herbicidal Compositions on Wheat and Barley

| Compound 1 TEA salt | Fenchlorazole-ethyl | Herbicide:Safener Ratio | TRZAS Ob | TRZAS Ex | HORVS Ob | HORVS Ex | GALAP Ob | GALAP Ex | KCHSC Ob | KCHSC Ex | LAMPU Ob | LAMPU Ex | MATCH Ob | MATCH Ex |
|---|---|---|---|---|---|---|---|---|---|---|---|---|---|---|
| 140 | 0 | | 26 | — | 16 | — | 100 | — | 94 | — | 99 | — | 80 | — |
| 0 | 140 | | 0 | — | 0 | — | 0 | — | — | — | — | — | — | — |
| 0 | 70 | | 0 | — | 0 | — | 0 | — | — | — | — | — | — | — |
| 0 | 35 | | 0 | — | 0 | — | 0 | — | — | — | — | — | — | — |
| 0 | 17.5 | | 0 | — | 0 | — | 0 | — | — | — | — | — | — | — |
| 140 | 140 | 1:1 | 0 | 26 | 0 | 16 | 100 | 100 | 98 | 94 | 100 | 99 | 65 | 80 |
| 140 | 70 | 2:1 | 0 | 26 | 0 | 16 | 100 | 100 | 99 | 94 | 100 | 99 | 68 | 80 |
| 140 | 35 | 4:1 | 0 | 26 | 0 | 16 | 100 | 100 | 94 | 94 | 100 | 99 | 78 | 80 |

| Compound 1 TEA salt | Fenchlorazole-ethyl | Herbicide:Safener Ratio | PAPRH Ob | PAPRH Ex | POLCO Ob | POLCO Ex | SASKR Ob | SASKR Ex | STEME Ob | STEME Ex | VERPE Ob | VERPE Ex | VIOTR Ob | VIOTR Ex |
|---|---|---|---|---|---|---|---|---|---|---|---|---|---|---|
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 99 | 100 | 88 | 88 | 99 | 94 | 88 | 85 | 73 | 69 |
| 140 | 70 | 2:1 | 100 | 100 | 94 | 100 | 89 | 88 | 98 | 94 | 88 | 85 | 75 | 69 |
| 140 | 35 | 4:1 | 100 | 100 | 83 | 100 | 88 | 88 | 80 | 94 | 89 | 85 | 75 | 69 |

TABLE 7

Safening Activity of Herbicidal Compositions on Wheat and Barley

| Compound 1 TEA salt | Fenclorim | Herbicide:Safener Ratio | TRZAS Ob | TRZAS Ex | HORVS Ob | HORVS Ex | GALAP Ob | GALAP Ex | KCHSC Ob | KCHSC Ex | LAMPU Ob | LAMPU Ex | MATCH Ob | MATCH Ex |
|---|---|---|---|---|---|---|---|---|---|---|---|---|---|---|
| 140 | 0 | | 26 | — | 16 | — | 100 | — | 94 | — | 99 | — | 80 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 6 | 26 | 4 | 16 | 100 | 100 | 95 | 94 | 100 | 99 | 78 | 80 |
| 140 | 70 | 2:1 | 7 | 26 | 8 | 16 | 100 | 100 | 93 | 94 | 100 | 99 | 77 | 80 |
| 140 | 35 | 4:1 | 8 | 26 | 5 | 16 | 100 | 100 | 89 | 94 | 100 | 99 | 60 | 80 |

| Compound 1 TEA salt | Fenclorim | Herbicide:Safener Ratio | PAPRH Ob | PAPRH Ex | POLCO Ob | POLCO Ex | SASKR Ob | SASKR Ex | STEME Ob | STEME Ex | VERPE Ob | VERPE Ex | VIOTR Ob | VIOTR Ex |
|---|---|---|---|---|---|---|---|---|---|---|---|---|---|---|
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 99 | 100 | 85 | 88 | 94 | 94 | 93 | 85 | 65 | 69 |
| 140 | 70 | 2:1 | 100 | 100 | 99 | 100 | 89 | 88 | 88 | 94 | 90 | 85 | 68 | 69 |
| 140 | 35 | 4:1 | 100 | 100 | 96 | 100 | 88 | 88 | 93 | 94 | 90 | 85 | 65 | 69 |

TABLE 8

Safening Activity of Herbicidal Compositions on Wheat and Barley

| Compound 1 TEA salt | Fluxofenim | Herbicide:Safener Ratio | TRZAS Ob | TRZAS Ex | HORVS Ob | HORVS Ex | GALAP Ob | GALAP Ex | KCHSC Ob | KCHSC Ex | LAMPU Ob | LAMPU Ex | MATCH Ob | MATCH Ex |
|---|---|---|---|---|---|---|---|---|---|---|---|---|---|---|
| 140 | 0 |  | 26 | — | 16 | — | 100 | — | 94 | — | 99 | — | 80 | — |
| 0 | 140 |  | 0 | — | 0 | — | 0 | — | — | — | — | — | — | — |
| 0 | 70 |  | 0 | — | 0 | — | 0 | — | — | — | — | — | — | — |
| 0 | 35 |  | 0 | — | 0 | — | 0 | — | — | — | — | — | — | — |
| 0 | 17.5 |  | 0 | — | 0 | — | 0 | — | — | — | — | — | — | — |
| 140 | 140 | 1:1 | 0 | 26 | 11 | 16 | 100 | 100 | 89 | 94 | 98 | 99 | 80 | 80 |
| 140 | 70 | 2:1 | 1 | 26 | 13 | 16 | 100 | 100 | 89 | 94 | 100 | 99 | 78 | 80 |
| 140 | 35 | 4:1 | 0 | 26 | 0 | 16 | 100 | 100 | 90 | 94 | 100 | 99 | 84 | 80 |

| Compound 1 TEA salt | Fluxofenim | Herbicide:Safener Ratio | PAPRH Ob | PAPRH Ex | POLCO Ob | POLCO Ex | SASKR Ob | SASKR Ex | STEME Ob | STEME Ex | VERPE Ob | VERPE Ex | VIOTR Ob | VIOTR Ex |
|---|---|---|---|---|---|---|---|---|---|---|---|---|---|---|
| 140 | 0 |  | 100 | — | 100 | — | 88 | — | 94 | — | 85 | — | 69 | — |
| 0 | 140 |  | 0 | — | 0 | — | 0 | — | 0 | — | 0 | — | 0 | — |
| 0 | 70 |  | 0 | — | 0 | — | 0 | — | 0 | — | 0 | — | 0 | — |
| 0 | 35 |  | 0 | — | 0 | — | 0 | — | 0 | — | 0 | — | 0 | — |
| 0 | 17.5 |  | 0 | — | 0 | — | 0 | — | 0 | — | 0 | — | 0 | — |
| 140 | 140 | 1:1 | 100 | 100 | 100 | 100 | 89 | 88 | 99 | 94 | 89 | 85 | 68 | 69 |
| 140 | 70 | 2:1 | 100 | 100 | 93 | 100 | 89 | 88 | 100 | 94 | 92 | 85 | 68 | 69 |
| 140 | 35 | 4:1 | 100 | 100 | 100 | 100 | 89 | 88 | 100 | 94 | 89 | 85 | 68 | 69 |

TABLE 9

Safening Activity of Herbicidal Compositions on Wheat and Barley

| Compound 1 TEA salt | Furilazole (MON 13900) | Herbicide:Safener Ratio | TRZAS Ob | TRZAS Ex | HORVS Ob | HORVS Ex | GALAP Ob | GALAP Ex | KCHSC Ob | KCHSC Ex | LAMPU Ob | LAMPU Ex | MATCH Ob | MATCH Ex |
|---|---|---|---|---|---|---|---|---|---|---|---|---|---|---|
| 140 | 0 |  | 26 | | 16 | | 100 | | 94 | | 99 | | 80 | |
| 0 | 140 |  | 0 | | 0 | | 0 | | 0 | | 0 | | 0 | |
| 0 | 70 |  | 0 | | 0 | | 0 | | 0 | | 0 | | 0 | |
| 0 | 35 |  | 0 | | 0 | | 0 | | 0 | | 0 | | 0 | |
| 0 | 17.5 |  | 0 | | 0 | | 0 | | 0 | | 0 | | 0 | |
| 140 | 140 | 1:1 | 6 | 26 | 4 | 16 | 100 | 100 | 86 | 94 | 100 | 99 | 70 | 80 |
| 140 | 70 | 2:1 | 8 | 26 | 9 | 16 | 100 | 100 | 89 | 94 | 100 | 99 | 93 | 80 |
| 140 | 35 | 4:1 | 5 | 26 | 7 | 16 | 100 | 100 | 87 | 94 | 100 | 99 | 85 | 80 |
| 140 | 17.5 | 8:1 | 2 | 26 | 13 | 16 | 100 | 100 | 85 | 94 | 100 | 99 | | 80 |

| Compound 1 TEA salt | Furilazole (MON 13900) | Herbicide:Safener Ratio | PAPRH Ob | PAPRH Ex | POLCO Ob | POLCO Ex | SASKR Ob | SASKR Ex | STEME Ob | STEME Ex | VERPE Ob | VERPE Ex | VIOTR Ob | VIOTR Ex |
|---|---|---|---|---|---|---|---|---|---|---|---|---|---|---|
| 140 | 0 |  | 100 | | 100 | | 88 | | 94 | | 85 | | 69 | |
| 0 | 140 |  | 0 | | 0 | | 0 | | 0 | | 0 | | 0 | |
| 0 | 70 |  | 0 | | 0 | | 0 | | 0 | | 0 | | 0 | |
| 0 | 35 |  | 0 | | 0 | | 0 | | 0 | | 0 | | 0 | |
| 0 | 17.5 |  | 0 | | 0 | | 0 | | 0 | | 0 | | 0 | |
| 140 | 140 | 1:1 | 100 | 100 | 94 | 100 | 92 | 88 | 85 | 94 | 78 | 85 | 73 | 69 |
| 140 | 70 | 2:1 | 100 | 100 | 97 | 100 | 90 | 88 | 90 | 94 | 82 | 85 | 73 | 69 |
| 140 | 35 | 4:1 | 100 | 100 | 93 | 100 | 91 | 88 | 83 | 94 | 83 | 85 | 73 | 69 |
| 140 | 17.5 | 8:1 | 100 | 100 | 95 | 100 | 90 | 88 | 83 | 94 | 80 | 85 | 75 | 69 |

TABLE 10

Safening Activity of Herbicidal Compositions on Wheat and Barley

| Application Rate (g/ha) | | | TRZAS | | HORVS | | GALAP | | KCHSC | | LAMPU | | MATCH | |
|---|---|---|---|---|---|---|---|---|---|---|---|---|---|---|
| Compound 1 TEA salt | Mefenpyr-diethyl | Herbicide:Safener Ratio | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | — | — | — | — | — | — |
| 0 | 70 | | 0 | — | 0 | — | 0 | — | — | — | — | — | — | — |
| 0 | 35 | | 0 | — | 0 | — | 0 | — | — | — | — | — | — | — |
| 0 | 17.5 | | 0 | — | 0 | — | 0 | — | — | — | — | — | — | — |
| 140 | 140 | 1:1 | 1 | 26 | 3 | 16 | 100 | 100 | 75 | 94 | 100 | 99 | 70 | 80 |
| 140 | 70 | 2:1 | 0 | 26 | 3 | 16 | 100 | 100 | 75 | 94 | 100 | 99 | 85 | 80 |
| 140 | 35 | 4:1 | 2 | 26 | 4 | 16 | 100 | 100 | 70 | 94 | 100 | 99 | 80 | 80 |

| Application Rate (g/ha) | | | PAPRH | | POLCO | | SASKR | | STEME | | VERPE | | VIOTR | |
|---|---|---|---|---|---|---|---|---|---|---|---|---|---|---|
| Compound 1 TEA salt | Mefenpyr-diethyl | Herbicide:Safener Ratio | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 98 | 100 | 94 | 88 | 87 | 94 | 88 | 85 | 75 | 69 |
| 140 | 70 | 2:1 | 100 | 100 | 95 | 100 | 90 | 88 | 88 | 94 | 88 | 85 | 75 | 69 |
| 140 | 35 | 4:1 | 100 | 100 | 90 | 100 | 88 | 88 | 88 | 94 | 83 | 85 | 70 | 69 |

TABLE 11

Safening Activity of Herbicidal Compositions on Wheat and Barley

| Application Rate (g/ha) | | | TRZAS | | HORVS | | GALAP | | KCHSC | | LAMPU | | MATCH | |
|---|---|---|---|---|---|---|---|---|---|---|---|---|---|---|
| Compound 1 TEA salt | Naphthalic anhydride | Herbicide:Safener Ratio | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | — | — | — | — | — | — |
| 0 | 70 | | 0 | — | 0 | — | 0 | — | — | — | — | — | — | — |
| 0 | 35 | | 0 | — | 0 | — | 0 | — | — | — | — | — | — | — |
| 0 | 17.5 | | 0 | — | 0 | — | 0 | — | — | — | — | — | — | — |
| 140 | 140 | 1:1 | 13 | 26 | 8 | 16 | 100 | 100 | 91 | 94 | 100 | 99 | 93 | 80 |
| 140 | 70 | 2:1 | 16 | 26 | 11 | 16 | 100 | 100 | 93 | 94 | 100 | 99 | 87 | 80 |
| 140 | 35 | 4:1 | 10 | 26 | 4 | 16 | 100 | 100 | 94 | 94 | 100 | 99 | 75 | 80 |

| Application Rate (g/ha) | | | PAPRH | | POLCO | | SASKR | | STEME | | VERPE | | VIOTR | |
|---|---|---|---|---|---|---|---|---|---|---|---|---|---|---|
| Compound 1 TEA salt | Naphthalic anhydride | Herbicide:Safener Ratio | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 99 | 100 | 88 | 88 | 94 | 94 | 87 | 85 | 78 | 69 |
| 140 | 70 | 2:1 | 100 | 100 | 100 | 100 | 89 | 88 | 95 | 94 | 85 | 85 | 75 | 69 |
| 140 | 35 | 4:1 | 100 | 100 | 98 | 100 | 87 | 88 | 98 | 94 | 88 | 85 | 70 | 69 |

TABLE 12

Safening Activity of Herbicidal Compositions on Wheat and Barley

| Application Rate (g/ha) | | | TRZAS | | HORVS | | GALAP | | KCHSC | | LAMPU | | MATCH | |
|---|---|---|---|---|---|---|---|---|---|---|---|---|---|---|
| Compound 1 TEA salt | Oxabetrinil | Herbicide:Safener Ratio | Ob | Ex | Ob | Ex | Ob | Ex | Ob | Ex | Ob | Ex | Ob | Ex |
| 140 | 0 | | 26 | — | 16 | — | 100 | — | 94 | — | 99 | — | 80 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 20 | 26 | 16 | 16 | 100 | 100 | 92 | 94 | 100 | 99 | 93 | 80 |
| 140 | 70 | 2:1 | 21 | 26 | 18 | 16 | 100 | 100 | 90 | 94 | 100 | 99 | 87 | 80 |
| 140 | 35 | 4:1 | 13 | 26 | 10 | 16 | 100 | 100 | 99 | 94 | 100 | 99 | 97 | 80 |

| Application Rate (g/ha) | | | PAPRH | | POLCO | | SASKR | | STEME | | VERPE | | VIOTR | |
|---|---|---|---|---|---|---|---|---|---|---|---|---|---|---|
| Compound 1 TEA salt | Oxabetrinil | Herbicide:Safener Ratio | Ob | Ex | Ob | Ex | Ob | Ex | Ob | Ex | Ob | Ex | Ob | Ex |
| 140 | 0 | | 100 | — | 100 | — | 88 | — | 94 | — | 85 | — | 69 | — |
| 0 | 140 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 140 | 140 | 1:1 | 100 | 100 | 98 | 100 | 94 | 88 | 100 | 94 | 92 | 85 | 73 | 69 |
| 140 | 70 | 2:1 | 100 | 100 | 97 | 100 | 90 | 88 | 100 | 94 | 89 | 85 | 80 | 69 |
| 140 | 35 | 4:1 | 100 | 100 | 97 | 100 | 89 | 88 | 89 | 94 | 88 | 85 | 73 | 69 |

TABLE 13

Safening Activity of Herbicidal Compositions on Wheat and Barley

| Application Rate (g/ha) | | | TRZAS | | HORVS | | MATCH | | VIOTR | |
|---|---|---|---|---|---|---|---|---|---|---|
| Compound 1 K salt | Glyphosate | Herbicide:Safener Ratio | Ob | Ex | Ob | Ex | Ob | Ex | Ob | Ex |
| 8.75 | 0 | | 5 | — | 1.7 | — | 50 | — | 20 | — |
| 17.5 | 0 | | 8 | — | 3.3 | — | 62 | — | 48 | — |
| 35 | 0 | | 27 | — | 6.7 | — | 57 | — | 42 | — |
| 0 | 52.5 | | 48 | — | 13 | — | 28 | — | 52 | — |
| 8.75 | 52.5 | 1:6 | 37 | 51 | 12 | 15 | 55 | 64 | 75 | 61 |
| 7.5 | 52.5 | 1:7 | 37 | 53 | 10 | 16 | 58 | 73 | 77 | 75 |
| 35 | 52.5 | 1:1.5 | 45 | 62 | 12 | 19 | 75 | 69 | 83 | 72 |

TABLE 14

Safening Activity of Herbicidal Compositions on Wheat and Barley

| Application Rate (g/ha) | | | HORVW | | TRZDU | | TRZAW | | LAMPU | | PAPRH | |
|---|---|---|---|---|---|---|---|---|---|---|---|---|
| Compound 1 Methyl ester | AD-67 | Herbicide:Safener Ratio | Ob | Ex | Ob | Ex | Ob | Ex | Ob | Ex | Ob | Ex |
| 35 | 0 | 0 | 50 | — | 42 | — | 35 | — | 97 | — | 97 | — |
| 0 | 4.4 | | 0 | — | 0 | — | 0 | — | 0 | — | 0 | — |
| 0 | 8.8 | | 0 | — | 0 | — | 0 | — | 0 | — | 0 | — |
| 0 | 17.5 | | 0 | — | 0 | — | 0 | — | 0 | — | 0 | — |
| 0 | 35 | | 0 | — | 0 | — | 0 | — | 0 | — | 0 | — |
| 35 | 35 | 1:1 | 30 | 50 | 22 | 42 | 12 | 35 | 97 | 97 | 95 | 97 |
| 35 | 17.5 | 2:1 | 13 | 50 | 20 | 42 | 13 | 35 | 100 | 97 | 100 | 97 |
| 35 | 8.8 | 4:1 | 13 | 50 | 18 | 42 | 17 | 35 | 100 | 97 | 100 | 97 |
| 35 | 4.4 | 8:1 | 15 | 50 | 13 | 42 | 13 | 35 | 100 | 97 | 100 | 97 |

TABLE 15

Safening Activity of Herbicidal Compositions on Wheat and Barley

Application Rate (g/ha)

| Compound 1 Methyl ester | Benoxacor | Herbicide:Safener Ratio | HORVW Ob | Ex | TRZDU Ob | Ex | TRZAW Ob | Ex | LAMPU Ob | Ex | PAPRH Ob | Ex |
|---|---|---|---|---|---|---|---|---|---|---|---|---|
| 35 | 0 | 0 | 50 | — | 42 | — | 35 | — | 97 | — | 97 | — |
| 0 | 4.4 | | 0 | — | 0 | — | 0 | — | 0 | — | 0 | — |
| 0 | 8.8 | | 0 | — | 0 | — | 0 | — | 0 | — | 0 | — |
| 0 | 17.5 | | 0 | — | 0 | — | 0 | — | 0 | — | 0 | — |
| 0 | 35 | | 0 | — | 0 | — | 0 | — | 0 | — | 0 | — |
| 35 | 35 | 1:1 | 15 | 50 | 18 | 42 | 15 | 35 | 100 | 97 | 100 | 97 |
| 35 | 17.5 | 2:1 | 15 | 50 | 17 | 42 | 18 | 35 | 100 | 97 | 100 | 97 |
| 35 | 8.8 | 4:1 | 13 | 50 | 25 | 42 | 22 | 35 | 100 | 97 | 100 | 97 |
| 35 | 4.4 | 8:1 | 10 | 50 | 20 | 42 | 20 | 35 | 100 | 97 | 100 | 97 |

TABLE 16

Safening Activity of Herbicidal Compositions on Wheat and Barley

Application Rate (g/ha)

| Compound 1 Methyl ester | 2-CBSU | Herbicide:Safener Ratio | HORVW Ob | Ex | TRZDU Ob | Ex | TRZAW Ob | Ex | LAMPU Ob | Ex | PAPRH Ob | Ex |
|---|---|---|---|---|---|---|---|---|---|---|---|---|
| 35 | 0 | 0 | 50 | — | 42 | — | 35 | — | 97 | — | 97 | — |
| 0 | 4.4 | | 0 | — | 0 | — | 0 | — | 0 | — | 0 | — |
| 0 | 8.8 | | 0 | — | 0 | — | 0 | — | 0 | — | 0 | — |
| 0 | 17.5 | | 0 | — | 0 | — | 0 | — | 0 | — | 0 | — |
| 0 | 35 | | 0 | — | 0 | — | 0 | — | 0 | — | 0 | — |
| 35 | 35 | 1:1 | 12 | 50 | 22 | 42 | 13 | 35 | 100 | 97 | 100 | 97 |
| 35 | 17.5 | 2:1 | 15 | 50 | 22 | 42 | 20 | 35 | 400 | 97 | 100 | 97 |
| 35 | 8.8 | 4:1 | 20 | 50 | 20 | 42 | 20 | 35 | 100 | 97 | 100 | 97 |
| 35 | 4.4 | 8:1 | 22 | 50 | 25 | 42 | 25 | 35 | 100 | 97 | 100 | 97 |

TABLE 17

Safening Activity of Herbicidal Compositions on Wheat and Barley

Application Rate (g/ha)

| Compound 1 Methyl ester | Daimuron | Herbicide:Safener Ratio | HORVW Ob | Ex | TRZDU Ob | Ex | TRZAW Ob | Ex | HORVS Ob | Ex | LAMPU Ob | Ex | PAPRH Ob | Ex |
|---|---|---|---|---|---|---|---|---|---|---|---|---|---|---|
| 35 | 0 | 0 | 50 | — | 42 | — | 35 | — | 33 | — | 97 | — | 97 | — |
| 0 | 4.4 | | 0 | — | 0 | — | 0 | — | 0 | — | 0 | — | 0 | — |
| 0 | 8.8 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 0 | 35 | | 0 | — | 0 | — | 0 | — | 0 | — | 0 | — | 0 | — |
| 35 | 35 | 1:1 | 3 | 50 | 7 | 42 | 10 | 35 | 18 | 33 | 100 | 97 | 95 | 97 |
| 35 | 17.5 | 2:1 | 15 | 50 | 12 | 42 | 10 | 35 | 12 | 33 | 100 | 97 | 100 | 97 |
| 35 | 8.8 | 4:1 | 20 | 50 | 15 | 42 | 10 | 35 | 12 | 33 | 100 | 97 | 100 | 97 |
| 35 | 4.4 | 8:1 | 20 | 50 | 15 | 42 | 15 | 35 | 15 | 33 | 100 | 97 | 100 | 97 |

TABLE 18

Safening Activity of Herbicidal Compositions on Wheat and Barley

Application Rate (g/ha)

| Compound 1 Methyl ester | Dichlormid | Herbicide:Safener Ratio | HORVW Ob | Ex | TRZDU Ob | Ex | TRZAW Ob | Ex | HORVS Ob | Ex | LAMPU Ob | Ex | PAPRH Ob | Ex |
|---|---|---|---|---|---|---|---|---|---|---|---|---|---|---|
| 35 | 0 | 0 | 50 | — | 42 | — | 35 | — | 33 | — | 97 | — | 97 | — |
| 0 | 4.4 | | 0 | — | 0 | — | 0 | — | 0 | — | 0 | — | 0 | — |
| 0 | 8.8 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 0 | 35 | | 0 | — | 0 | — | 0 | — | 0 | — | 0 | — | 0 | — |

TABLE 18-continued

Safening Activity of Herbicidal Compositions on Wheat and Barley

| Application Rate (g/ha) | | | HORVW | | TRZDU | | TRZAW | | HORVS | | LAMPU | | PAPRH | |
|---|---|---|---|---|---|---|---|---|---|---|---|---|---|---|
| Compound 1 Methyl ester | Dichlormid | Herbicide:Safener Ratio | Ob | Ex | Ob | Ex | Ob | Ex | Ob | Ex | Ob | Ex | Ob | Ex |
| 35 | 35 | 1:1 | 5 | 50 | 13 | 42 | 10 | 35 | 13 | 33 | 100 | 97 | 98 | 97 |
| 35 | 17.5 | 2:1 | 8 | 50 | 13 | 42 | 17 | 35 | 15 | 33 | 100 | 97 | 100 | 97 |
| 35 | 8.8 | 4:1 | 10 | 50 | 18 | 42 | 18 | 35 | 18 | 33 | 100 | 97 | 100 | 97 |
| 35 | 4.4 | 8:1 | 27 | 50 | 15 | 42 | 22 | 35 | 20 | 33 | 100 | 97 | 100 | 97 |

TABLE 19

Safening Activity of Herbicidal Compositions on Wheat and Barley

| Application Rate (g/ha) | | | HORVW | | TRZDU | | TRZAW | | HORVS | | LAMPU | | PAPRH | |
|---|---|---|---|---|---|---|---|---|---|---|---|---|---|---|
| Compound 1 Methyl ester | Dicyclonon | Herbicide:Safener Ratio | Ob | Ex | Ob | Ex | Ob | Ex | Ob | Ex | Ob | Ex | Ob | Ex |
| 35 | 0 | 0 | 50 | — | 42 | — | 35 | — | 33 | — | 97 | — | 97 | — |
| 0 | 4.4 | | 0 | — | 0 | — | 0 | — | 0 | — | 0 | — | 0 | — |
| 0 | 8.8 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 0 | 35 | | 0 | — | 0 | — | 0 | — | 0 | — | 0 | — | 0 | — |
| 35 | 35 | 1:1 | 20 | 50 | 27 | 42 | 25 | 35 | 22 | 33 | 100 | 97 | 100 | 97 |
| 35 | 17.5 | 2:1 | 15 | 50 | 23 | 42 | 22 | 35 | 25 | 33 | 100 | 97 | 100 | 97 |
| 35 | 8.8 | 4:1 | 15 | 50 | 23 | 42 | 22 | 35 | 23 | 33 | 100 | 97 | 100 | 97 |
| 35 | 4.4 | 8:1 | 18 | 50 | 27 | 42 | 27 | 35 | 20 | 33 | 100 | 97 | 100 | 97 |

TABLE 20

Safening Activity of Herbicidal Compositions on Wheat and Barley

| Application Rate (g/ha) | | | TRZAS | | HORVW | | TRZDU | | TRZAW | | HORVS | | LAMPU | | PAPRH | |
|---|---|---|---|---|---|---|---|---|---|---|---|---|---|---|---|---|
| Compound 1 Methyl ester | Fenchlorazole | Herbicide:Safener Ratio | Ob | Ex | Ob | Ex | Ob | Ex | Ob | Ex | Ob | Ex | Ob | Ex | Ob | Ex |
| 35 | 0 | 0 | 50 | — | 50 | — | 42 | — | 35 | — | 33 | — | 97 | — | 97 | — |
| 0 | 4.4 | | 0 | — | 0 | — | 0 | — | 0 | — | 0 | — | 0 | — | 0 | — |
| 0 | 8.8 | | 0 | — | 0 | — | 0 | — | 0 | — | 0 | — | 0 | — | 0 | — |
| 0 | 17.5 | | 0 | — | 0 | — | 0 | — | 0 | — | 0 | — | 0 | — | 0 | — |
| 0 | 35 | | 0 | — | 0 | — | 0 | — | 0 | — | 0 | — | 0 | — | 0 | — |
| 35 | 35 | 1:1 | 0 | 50 | 0 | 50 | 0 | 42 | 0 | 35 | 0 | 33 | 100 | 97 | 100 | 97 |
| 35 | 17.5 | 2:1 | 0 | 50 | 0 | 50 | 0 | 42 | 0 | 35 | 0 | 33 | 100 | 97 | 100 | 97 |
| 35 | 8.8 | 4:1 | 0 | 50 | 0 | 50 | 0 | 42 | 0 | 35 | 0 | 33 | 100 | 97 | 100 | 97 |
| 35 | 4.4 | 8:1 | 0 | 50 | 0 | 50 | 0 | 42 | 0 | 35 | 0 | 33 | 100 | 97 | 100 | 97 |

TABLE 21

Safening Activity of Herbicidal Compositions on Wheat and Barley

| Application Rate (g/ha) | | | TRZAS | | HORVW | | TRZDU | | TRZAW | | HORVS | | LAMPU | | PAPRH | |
|---|---|---|---|---|---|---|---|---|---|---|---|---|---|---|---|---|
| Compound 1 Methyl ester | Isoxadifen | Herbicide:Safener Ratio | Ob | Ex | Ob | Ex | Ob | Ex | Ob | Ex | Ob | Ex | Ob | Ex | Ob | Ex |
| 35 | 0 | 0 | 50 | — | 50 | — | 42 | — | 35 | — | 33 | — | 97 | — | 97 | — |
| 0 | 4.4 | | 0 | — | 0 | — | 0 | — | 0 | — | 0 | — | 0 | — | 0 | — |
| 0 | 8.8 | | 0 | — | 0 | — | 0 | — | 0 | — | 0 | — | 0 | — | 0 | — |
| 0 | 17.5 | | 0 | — | 0 | — | 0 | — | 0 | — | 0 | — | 0 | — | 0 | — |

TABLE 21-continued

Safening Activity of Herbicidal Compositions on Wheat and Barley

| Application Rate (g/ha) | | | | | | | | | | | | | | | |
|---|---|---|---|---|---|---|---|---|---|---|---|---|---|---|---|
| Compound 1 | | Herbicide:Safener | TRZAS | | HORVW | | TRZDU | | TRZAW | | HORVS | | LAMPU | | PAPRH | |
| Methyl ester | Isoxadifen | Ratio | Ob | Ex | Ob | Ex | Ob | Ex | Ob | Ex | Ob | Ex | Ob | Ex | Ob | Ex |
| 0 | 35 | | 0 | — | 0 | — | 0 | — | 0 | — | 0 | — | 0 | — | 0 | — |
| 35 | 35 | 1:1 | 0 | 50 | 5 | 50 | 12 | 42 | 0 | 35 | 0 | 33 | 98 | 97 | 100 | 97 |
| 35 | 17.5 | 2:1 | 3.3 | 50 | 12 | 50 | 17 | 42 | 3.3 | 35 | 5 | 33 | 98 | 97 | 100 | 97 |
| 35 | 8.8 | 4:1 | 33 | 50 | 37 | 50 | 32 | 42 | 13 | 35 | 15 | 33 | 97 | 97 | 98 | 97 |
| 35 | 4.4 | 8:1 | 42 | 50 | 42 | 50 | 37 | 42 | 17 | 35 | 17 | 33 | 99 | 97 | 100 | 97 |

TABLE 22

Safening Activity of Herbicidal Compositions on Wheat and Barley

| Application Rate (g/ha) | | | | | | | | | | | | | | | |
|---|---|---|---|---|---|---|---|---|---|---|---|---|---|---|---|
| Compound 1 | Mefenpyr- | Herbicide:Safener | TRZAS | | HORVW | | TRZDU | | TRZAW | | HORVS | | LAMPU | | PAPRH | |
| Methyl ester | diethyl | Ratio | Ob | Ex | Ob | Ex | Ob | Ex | Ob | Ex | Ob | Ex | Ob | Ex | Ob | Ex |
| 35 | 0 | 0 | 50 | — | 50 | — | 42 | — | 35 | — | 33 | — | 97 | — | 97 | — |
| 0 | 4.4 | | 0 | — | 0 | — | 0 | — | 0 | — | 0 | — | 0 | — | 0 | — |
| 0 | 8.8 | | 0 | — | 0 | — | 0 | — | 0 | — | 0 | — | 0 | — | 0 | — |
| 0 | 17.5 | | 0 | — | 0 | — | 0 | — | 0 | — | 0 | — | 0 | — | 0 | — |
| 0 | 35 | | 0 | — | 0 | — | 0 | — | 0 | — | 0 | — | 0 | — | 0 | — |
| 35 | 35 | 1:1 | 0 | 50 | 0 | 50 | 0 | 42 | 0 | 35 | 0 | 33 | 97 | 97 | 100 | 97 |
| 35 | 17.5 | 2:1 | 0 | 50 | 0 | 50 | 0 | 42 | 0 | 35 | 0 | 33 | 96 | 97 | 97 | 97 |
| 35 | 8.8 | 4:1 | 0 | 50 | 0 | 50 | 0 | 42 | 0 | 35 | 0 | 33 | 98 | 97 | 98 | 97 |
| 35 | 4.4 | 8:1 | 0 | 50 | 0 | 50 | 0 | 42 | 0 | 35 | 0 | 33 | 98 | 97 | 100 | 97 |

TRZAS = *Triticum aestivum* (spring wheat)
HORVS = *Hordeum vulgare* (spring barley)
GALAP = *Galium aparine* (cleavers)
KCHSC = *Kochia scoparia* (kochia)
LAMPU = *Lamium purpureum* (purple deadnettle)
MATCH = *Matricaria chamomila* (scented mayweed)
Ob = Observed values
g/ha = grams/hectare
Herbicide:Safener Ratio = Ratio herbicide to safener
PAPRH = *Papaver rhoeas* (corn poppy)
POLCO = *Polygonum convolvulus* (wild buckwheat)
SASKR = *Salsola iberica* (Russian thistle)
STEME = *Stellaria media* (common chickweed)
VERPE = *Veronica persica* (bird's-eye speedwell)
VIOTR = *Viola tricolor* (wild pansy)
Ex = Expected values

What is claimed is:

1. A composition for protecting wheat and barley from the harmful effects of a 6-(trisubstituted phenyl)-4-amino-2-pyridinecarboxylate herbicide, comprising a combination of a 6-(trisubstituted phenyl)-4-amino-2-pyridinecarboxylate herbicide according to the formula (I):

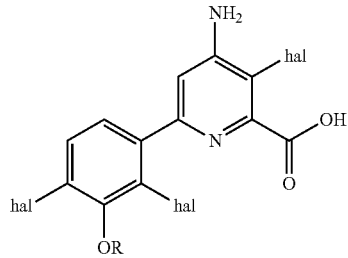

(I)

wherein hal represents F, Cl or Br, and R represents methyl or ethyl, and its agriculturally acceptable salt, ester and amide derivatives, and a safener or a compatible herbicide capable of safening, selected from the group consisting of AD67, benoxacor, 2-CBSU, daimuron, dichlormid, dicyclonon, fenchlorazole-ethyl, fenclorim, fluxofenim, furilazole, isoxadifenethyl, mefenpyr-diethyl, naphthalic anhydride, oxabetrinil and mixtures thereof, wherein the weight ratio of the 6-(trisubstituted phenyl)-4-amino-2-pyridinecarboxylate herbicide to the safener or the compatible herbicide capable of safening in the combination is from about 2:1 to about 32:1; and wherein the combination exhibits an observed safening effect on the 6-(trisubstituted phenyl)-4-amino-2-pyridinecarboxylate herbicide that is greater than the expected safening effect.

2. The composition of claim 1 in which the 6-(trisubstituted phenyl)-4-amino-2-pyridinecarboxylate herbicide is a 4-amino-3-chloro-6-(4-chloro-2-fluoro-3-methoxyphenyl)-

2-pyridinecarboxylic acid derivative or a 4-amino-3-chloro-6-(2,4-dichloro-3-methoxy-phenyl)-2-pyridinecarboxylic acid derivative.

3. The composition of claim 1, wherein the herbicide of formula (I) is

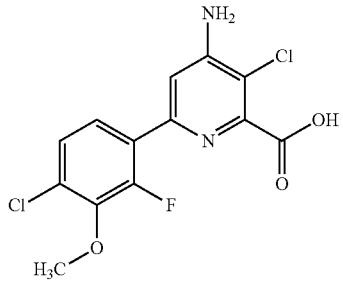 [SMILES: COc1c(Cl)ccc(-c2cc(N)c(Cl)c(C(=O)O)n2)c1F]

or its methyl ester or triethylammonium salt.

4. The composition of claim 1, wherein the herbicide of formula (I) is

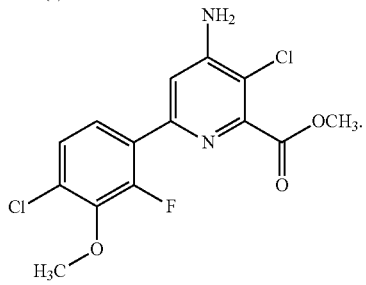

5. The composition of claim 2, wherein the herbicide of formula (I) is

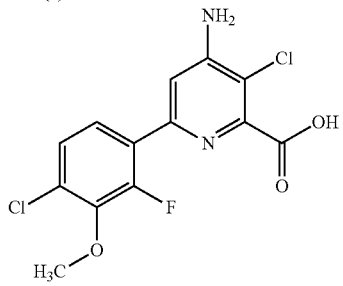

or its methyl ester or triethylammonium salt.

6. The composition of claim 2, wherein the herbicide of formula (I) is

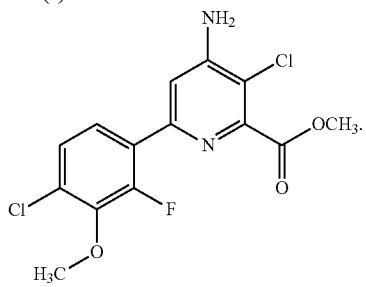

7. A method of protecting wheat and barley from the harmful effects of a 6-(trisubstituted phenyl)-4-amino-2-pyridinecarboxylate herbicide comprising the step of contacting the wheat and barley with, or applying to the area under cultivation of wheat and barley a combination of a 6-(trisubstituted phenyl)-4-amino-2-pyridinecarboxylate herbicide according to the formula (I):

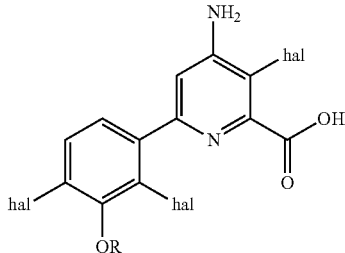

wherein hal represents F, Cl or Br, and R represents methyl or ethyl, and its agriculturally acceptable salt, ester and amide derivatives, and a safener, or a compatible herbicide capable of safening, selected from the group consisting of AD67, benoxacor, 2-CBSU, daimuron, dichlormid, dicyclonon, fenchlorazole-ethyl, fenclorim, fluxofenim, furilazole, isoxadifenethyl, mefenpyr-diethyl, naphthalic anhydride, oxabetrinil and mixtures thereof wherein the weight ratio of the 6-(trisubstituted phenyl)-4-amino-2-pyridinecarboxylate herbicide to the safener or compatible herbicide capable of safening in the combination is from about 2:1 to about 32:1; and wherein the combination exhibits an observed safening effect that is greater than the expected safening effect.

8. The method of claim 7, wherein the herbicide of formula (I) is:

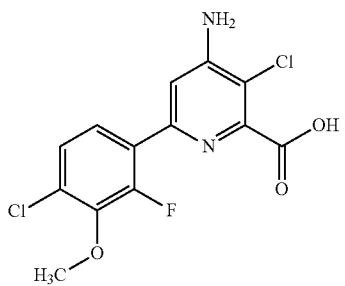 [SMILES: COc1c(Cl)ccc(-c2cc(N)c(Cl)c(C(=O)O)n2)c1F]

or its methyl ester or triethylammonium salt.

9. The method of claim 7, wherein the herbicide of formula (I) is

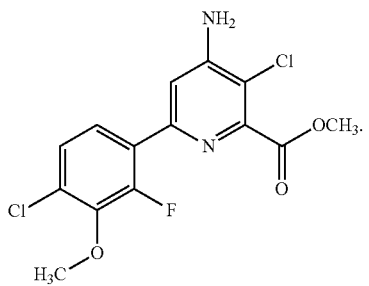 [SMILES: COC(=O)c1nc(-c2ccc(Cl)c(OC)c2F)cc(N)c1Cl]

10. The method of claim 7, wherein the wheat and barley is *Triticum aestivum* or *Hordeum vulgare*.

11. A composition which is effective in protecting wheat and barley from the harmful effects of a 6-(trisubstituted phenyl)-4-amino-2-pyridinecarboxylate herbicide, comprising a combination of a 6-(trisubstituted phenyl)-4-amino-2-pyridinecarboxylate herbicide according to the formula (I):

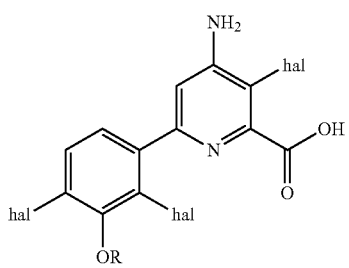

(I)

wherein hal represents F, Cl or Br, and R represents methyl or ethyl, and its agriculturally acceptable salt, ester and amide derivatives, and a 2-CBSU safener; wherein the ratio range of the formula (I) to the safener is from about 2:1 to about 32:1, and wherein the combination exhibits an observed safening effect that is greater than the expected safening effect.

12. A method of applying the composition of claim 11 for protecting wheat and barley which comprises contacting the wheat and barley with, or applying to the area under cultivation of wheat and barley, the composition.

13. The composition of claim 11, wherein the weight ratio of the 6-(trisubstituted phenyl)-4-amino-2-pyridinecarboxylate herbicide to 2-CBSU is from about 16:1 to about 2:1.

14. The composition of claim 11, wherein the weight ratio of the 6-(trisubstituted phenyl)-4-amino-2-pyridinecarboxylate herbicide to 2-CBSU is from about 4:1 to about 2:1.

15. The composition of claim 11, wherein the weight ratio of the 6-(trisubstituted phenyl)-4-amino-2-pyridinecarboxylate herbicide to 2-CBSU is from about 1:1 to about 2:1.

16. The composition of claim 11, wherein the weight ratio of the 6-(trisubstituted phenyl)-4-amino-2-pyridinecarboxylate herbicide to 2-CBSU is from greater than 2:1 to about 8:1.

17. The method of claim 12, wherein the weight ratio of the 6-(trisubstituted phenyl)-4-amino-2-pyridinecarboxylate herbicide to 2-CBSU is from about 16:1 to about 2:1.

18. The method of claim 12, wherein the weight ratio of the 6-(trisubstituted phenyl)-4-amino-2-pyridinecarboxylate herbicide to 2-CBSU is from about 4:1 to about 2:1.

19. The method of claim 12, wherein the weight ratio of the 6-(trisubstituted phenyl)-4-amino-2-pyridinecarboxylate herbicide to 2-CBSU is from about 2:1 to about 8:1.

20. The method of claim 12, wherein the weight ratio of the 6-(trisubstituted phenyl)-4-amino-2-pyridinecarboxylate herbicide to 2-CBSU is from greater than 2:1 to about 8:1.

\* \* \* \* \*

UNITED STATES PATENT AND TRADEMARK OFFICE
CERTIFICATE OF CORRECTION

| | |
|---|---|
| PATENT NO. | : 8,921,267 B2 |
| APPLICATION NO. | : 13/919416 |
| DATED | : December 30, 2014 |
| INVENTOR(S) | : Norbert Satchivi |

It is certified that error appears in the above-identified patent and that said Letters Patent is hereby corrected as shown below:

In the Claims

In Claim 15, Column 32, Line 9, should read:

from about 2:1 to about 8:1

Signed and Sealed this
Twenty-first Day of April, 2015

Michelle K. Lee
*Director of the United States Patent and Trademark Office*